(12) United States Patent
Ueda et al.

(10) Patent No.: US 6,207,434 B1
(45) Date of Patent: Mar. 27, 2001

(54) PROCESS FOR THE DEACYLATION OF CYCLIC LIPOPEPTIDES

(75) Inventors: Satoshi Ueda, Ama-gun; Miho Tanaka, Tsuchiura; Masami Ezaki, Tsukuba; Kazutoshi Sakamoto, Tsuchiura; Seiji Hashimoto, Tsukuba; Nobutaka Oohata; Masaru Tsuboi, both of Inazawa; Michio Yamashita, Tsukuba, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/142,045

(22) PCT Filed: Mar. 16, 1997

(86) PCT No.: PCT/JP97/00692

§ 371 Date: Sep. 3, 1998

§ 102(e) Date: Sep. 3, 1998

(87) PCT Pub. No.: WO97/32975

PCT Pub. Date: Sep. 12, 1997

(30) Foreign Application Priority Data

Mar. 8, 1996 (JP) ................................. 8-051386
Jul. 24, 1996 (JP) ................................. 8-194207

(51) Int. Cl.$^7$ ........................................... C12N 9/14
(52) U.S. Cl. ...................... 435/195; 435/253.5; 435/68.1
(58) Field of Search ................................... 435/195, 196, 435/814, 815, 253.5, 68.1

(56) References Cited

U.S. PATENT DOCUMENTS 4,396,543 * 8/1983 Debono ............................ 260/112.5
5,573,936 * 11/1996 Kreuzman ............................ 435/196

OTHER PUBLICATIONS

Boeck et al., J. Antibiotics, 1988, vol. 41, No. 8, pp. 1085–1092.*

* cited by examiner

*Primary Examiner*—Irene Marx
(74) *Attorney, Agent, or Firm*—Oblon, Spivak, McClelland, Maier & Neustadt, P.C.

(57) ABSTRACT

There is provided a cyclic lipopeptide acylase which is capable of deacylating the acyl side chain of a cyclic lipopeptide compound, e.g. Substance FR901379 or its analog, of the general formula [I] with effectiveness as well a method of producing a cyclic peptide compound which comprises using the acylase.

9 Claims, No Drawings

PROCESS FOR THE DEACYLATION OF CYCLIC LIPOPEPTIDES

This Appln. is a 371 of PCT/JP97/00000 Mar. 6, 1997.

TECHNICAL FIELD

The present invention relates to enzyme technology.

The present invention relates to a novel acylase capable of deacylating the acyl side chain of a cyclic lipopeptide compound and to a deacylation method using the same.

More particularly, the invention relates to a novel acylase adapted to deacylate the acyl side chain of Substance FR901379 (described in Japanese Kokai Tokkyo Koho H3-184921), which is produced by the microorganism Coleophoma sp. F-11899 (FERM BP-2635), or an analog of Substance FR901379 and to a deacylation method using the same.

BACKGROUND ART

There has been a standing need for an acylase capable of deacylating the acyl side chain of a cyclic lipopeptide compound, specifically said Substance FR901379 or analog, with good efficiency.

DISCLOSURE OF THE INVENTION

The inventors of the present invention did an extensive research in search of a novel acylase capable of deacylating the acyl side chain of a cyclic lipopeptide represented by Substance FR901379 or its analogs such as Echinocandin B and Aculeacin A. As a result, they discovered an acylase produced by *Streptomyces anulatus* and succeeded in effective achievement of the objective deacylation.

The above novel cyclic lipopeptide acylase and the deacylation method using the same are now described with reference to their salient features.

First, the cyclic lipopeptide acylase-producing microorganism is described.

The novel cyclic lipopeptide acylase-producing microorganism includes but is not limited to *Streptomyces anulatus* No. 4811, *Streptomyces anulatus* No. 8703, and Streptomyces sp. 6907, all of which belong to the genus Streptomyces.

The characteristics of those strains are now described.

The novel cyclic lipopeptide acylase-producing strain named *Streptomyces anulatus* No. 4811 (herein after referred to briefly as Strain No. 4811) was isolated for the first time from a soil sample collected in Fukushima Prefecture. The bacteriological characteristics of this Strain No. 4811 are now described.

Cultural Characteristics

The cultural characteristics of Strain No. 4811 on yeast extract-malt extract agar, oatmeal agar, inorganic salts-starch agar, glycerin-asparagine agar, peptone-yeast extract-iron agar, and tyrosine agar after incubation at 30° C. for 14 days and the light and scanning electron microscopic observation of the respective growths are summarized in Table 1. The color descriptions given below correspond to the nomenclature defined in Methuen Handbook of Colour, Methuen, London, 1978.

TABLE 1

Cultural characteristics of Strain NO. 4811

| Medium | Cultural characteristics |
|---|---|
| Yeast extract-malt extract agar (ISP-2) | G: good<br>A: abundant, yellowish gray (2B2)<br>R: brown (7F4)<br>S: scanty, brown |
| Oatmeal agar (ISP-3) | G: good-moderate<br>A: abundant, yellowish gray (2C3)<br>R: brown (7F4)<br>S: trace, brown |
| Inorganic salts-Starch agar (ISP-4) | G: good<br>A: abundant, yellowish gray (2C3)<br>R: yellowish brown (5E4)<br>S: none |
| Glycerin-asparagine agar (ISP-5) | G: good<br>A: abundant, yellowish gray (2C3)<br>R: brown (6E4)<br>S: none |
| Peptone-yeast extract-iron agar (ISP-6) | G: moderate<br>A: poor, white<br>R: light brown (6D5)<br>S: none |
| Tyrosine agar (ISP-7) | G: moderate<br>A: moderate, yellowish gray (2B2)<br>R: brown (7F4)<br>S: none |

Codes: G: growth, A: aerial mycelium, R: reverse side color, S: soluble pigment

The color of the aerial mycelium was yellowish gray to greenish gray, the reverse side color of growth was yellowish brown to brown, the soluble pigment was light brown, and neither intracellular pigments nor soluble pigments were pH-sensitive. No melanoid pigments were produced.

Physiological Characteristics

The physiological characteristics of Strain No. 4811 are summarized in Table 2.

TABLE 2

Physiological characteristics of Strain No. 4811

| Test item | Result |
|---|---|
| Temperature range for growth | 4.0–35.0° C. |
| Liquefaction of gelatin | + |
| Coagulation of milk | ± |
| Peptonization of milk | + |
| Hydrolysis of starch | + |
| Production of Melanoid pigments | − |
| Carbon utilization: | |
| D-glucose | + |
| L-arabinose | + |
| D-xylose | + |
| Inositol | − |
| Mannitol | + |
| D-fructose | + |
| L-rhamnose | ± |
| Sucrose | − |
| Raffinose | − |

+: positive, ±: weakly positive, −: negative

The vegetative mycelium of Strain No. 4811 developed well and branched irregularly but not fragmented. The aerial mycelium extending from the vegetative mycelium branched monopodially to form elongated spore chains. The spore chain morphology of the aerial mycelium was straight-flexuous, thus belonging to the RF type according to the classification of Pridham et al. (Pridham, T. G. et al.: Appl. Microbiol., 6:54, 1958). Each spore chain consisted of 20 or more spores. The spores were smooth-surfaced (glabrous) and cylindrical. The spore size was 0.5~0.7×0.7~1.1 μm.

None of sclerotium, sporangium, and zoospore was observed.

Cell Wall Type

As to the cell wall amino acid composition, the whole-cell lysate was analyzed by the method of Becker et al. (Becker, B., M. P. Lechevalier, R. E. Gordon and H. A. Lechevalier: Rapid differentiation between Nocardia and Streptomyces by paper chromatography of whole-cell hydrolysates: Appl. Microbiol., 12:421–423, 1964) and the method of Yamaguchi (Yamaguchi, T.: Comparison of the cell wall composition of morphologically distinct actinomycetes: J. Bacteriol., 89:444–453, 1965). The result indicated the existence of LL-diaminopimelic acid. Therefore, the cell wall of this strain was considered to be of Type I.

Based on the above morphological observation and chemical analysis, Strain No. 4811 was considered to belong to the genus Streptomyces according to the taxonomic classification of Pridham et al. (Pridham, T. G. et al: Appl. Microbiol., 6:54, 1958). Accordingly, the characteristics of this strain were compared with those of Streptomyces species as described in the literature, namely Shirling et al. (Shirling, E. B. and D. Gottlieb: Cooperative Description of Type Culture of Streptomyces. 2. Species description from first study, Intern. J. Syst. Bacteriol., 18:69–189, 1968; Shirling, E. B. and D. Gottlieb: Cooperative Description of Type Culture of Streptomyces. 3. Additional species descriptions from first and second studies, Intern. J. Syst. Bacteriol., 18:279–392, 1968; Shirling, E. B. and D. Gottlieb: Cooperative Description of Type Culture of Streptomyces. 4. Species descriptions from second, third and forth studies, Intern. J. Syst. Bacteriol., 19:391–512, 1969); Skerman et al. (Skerman, V. B., V. McGowan and P. H. A. Sneath: Approved List of Bacterial Names, Amended Edition, American Society for Microbiology, Washington, D.C., 1989); and Moore et al. (Moore, W. E., E. P. Cato and L. V. H. Moore: Index of Bacterial and Yeast Nomencultural Changes, American Society for Microbiology, Washington D.C., 1992). The comparison indicated that the characteristics of *Streptomyces anulatus* so described were substantially identical to the characteristics of this strain. Accordingly, this Strain No. 4811 was identified as *Streptomyces anulatus* and named *Streptomyces anulatus* No. 4811.

This *Streptomyces anulatus* No. 4811 was originally deposited with National Institute of Bioscience and Human Technology (NIBH, 1–3, Higashi 1-chome, Tsukuba-shi, Ibaraki, Japan) (ZIP code 305) on Dec. 27, 1995 under the accession number of FERM P-15377 and subsequently converted to deposit according to the Budapest Treaty as of Feb. 3, 1997 under the accession number of FERM BP-5808.

The novel cyclic lipopeptide acylase-producing strain named *Streptomyces anulatus* No. 8703 (herein after referred to briefly as Strain No. 8703) was isolated for the first time from a soil sample collected in Fukushima Prefecture. The bacteriological characteristics of this Strain No. 8703 are now described.

Cultural Characteristics

The cultural characteristics of Strain No. 8703 on yeast extract-malt extract agar, oatmeal agar, inorganic salts-starch agar, glycerin-asparagine agar, peptone-yeast extract-iron agar, and tyrosine agar after incubation at 30° C. for 14 days and the light and scanning electron microscopic observations of the respective growths are summarized in Table 3. The color descriptions given below correspond to the nomenclature defined in Methuen Handbook of Colour, Methuen, London, 1978.

TABLE 3

Cultural characteristics of Strain No. 8703

| Medium | Cultural characteristics |
|---|---|
| Yeast extract-malt extract agar (ISP-2) | G: good<br>A: abundant, yellowish gray (2B2)<br>R: gray brown (5F4)<br>S: none |
| Oatmeal agar (ISP-3) | G: moderate<br>A: abundant, yellowish gray (2C3)<br>R: gray brown (4C4)<br>S: none |
| Inorganic salts-starch agar (ISP-4) | G: good<br>A: abundant, yellowish gray (2C3)<br>R: dark gray (1F6)<br>S: none |
| Glycerin-asparagine agar (ISP-5) | G: good<br>A: abundant, yellowish gray (2C3)<br>R: olive brown (4E5)<br>S: none |
| Peptone-yeast extract-iron agar (ISP-6) | G: moderate<br>A: poor, white<br>R: yellowish brown (5D5)<br>S: none |
| Tyrosine agar (ISP-7) | G: moderate<br>A: moderate, yellowish gray (2B2)<br>R: brown (7F4)<br>S: none |

Codes: G: growth, A: aerial mycelium, R: reverse side color, S: soluble pigment

The color of the aerial mycelium was yellowish gray to greenish gray, the reverse side color of growth was yellowish brown to brown, the soluble pigment was light brown, and neither intracellular pigments nor soluble pigments were pH-sensitive. Melanoid pigments were produced in tryptone-yeast extract broth, peptone-yeast extract-iron agar, and tyrosine agar.

Physiological Characteristics

The physiological characteristics of Strain No. 8703 are summarized in Table 4.

TABLE 4

Physiological characteristics of Strain No. 8703

| Test item | Result |
|---|---|
| Temperature range for growth | 4.0–35.0° C. |
| Liquefaction of gelatin | + |
| Coagulation of milk | ± |
| Peptonization of milk | + |
| Hydrolysis of starch | + |
| Production of Melanoid pigments | − |
| Carbon utilization: | |
| D-glucose | + |
| L-arabinose | + |
| D-xylose | + |
| Inositol | − |
| Mannitol | + |
| D-fructose | + |
| L-rhamnose | + |
| Sucrose | − |
| Raffinose | − |

+: positive, ±: weakly positive, −: negative

This strain did not utilize inositol, sucrose, and raffinose. It peptonized milk. The temperature range for growth was 4.0–35° C.

The vegetative mycelium of Strain No. 8703 was developed well and branched irregularly but was not fragmented. The aerial mycelium extending from the vegetative mycelium branched monopodially to form elongated spore chains. The spore chain morphology of the aerial mycelium was straight-flexuous, thus, belonging to the RF type according to the classification of Pridham et al. (Pridham, T. G. et al.: Appl. Microbiol., 6:54, 1958). Each spore chain consisted of 20 or more spores. The spore was smooth-surfaced and cylindrical. The spore size was 0.5~0.8×0.6~1.1 μm. None of sclerotium, sporangium, and zoospore was observed.

Cell Wall Type

As to the cell wall amino acid composition, the whole-cell lysate was analyzed by the method of Becker et al. (Becker, B., M. P. Lechevalier, R. E. Gordon and H. A. Lechevalier: Rapid differentiation between Nocardia and Streptomyces by paper chromatography of whole-cell hydrolysates: Appl. Microbiol., 12:421–423, 1964) and the method of Yamaguchi (Yamaguchi, T.: Comparison of the cell wall composition of morphologically distinct actinomycetes: J. Bacteriol., 89:444–453, 1965). The analysis indicated the existence of LL-diaminopimelic acid. Therefore, the cell wall of this strain is considered to be of Type I.

Based on the above morphological observation and chemical analysis, Strain No. 8703 was considered to belong to the genus Streptomyces according to the taxonomic classification of Pridham et al. (Pridham, T. G. et al: Appl. Microbiol., 6:54, 1958). Accordingly, the characters of this strain were compared with those of Streptomyces species as described in the literature, namely Shirling et al. (Shirling E. B. and D. Gottlieb: Cooperative Description of Type Culture of Streptomyces. 2. Species descriptions from first study, Intern. J. Syst. Bacteriol., 18:69–189, 1968; Shirling, E. B. and D. Gottlieb: Cooperative Description of Type Culture of Streptomyces. 3. Additional species descriptions from first and second studies., Intern. J. Syst. Bacteriol., 18:279–392, 1968; Shirling, E. B. and D. Gottlieb: Cooperative Description of Type Culture of Streptomyces. 4. Species descriptions from second, third and forth studies, Intern. J. Syst. Bacteriol., 19:391–521, 1969); Skerman et al. (Skerman, V. B., V. McGowan and P. H. A. Sneath: Approved List of Bacterial Names, Amended Edition, American Society for Microbiology, Washington D.C., 1989); and Moore et al. (Moore, W. E., E. P. Cato and L. V. H. Moore: Index of Bacterial and Yeast Nomencultural Changes, American Society for Microbiology, Washington D.C., 1992). The comparison indicated that the characteristics of *Streptomyces anulatus* so described were substantially identical to the characteristics of this strain. Accordingly, this Strain No. 8703 was identified as *Streptomyces anulatus* and named *Streptomyces anulatus* No. 8703.

This *Streptomyces anulatus* No. 8703 was originally deposited with National Institute of Bioscience and Human Technology (NIBH, 1–3, Higashi 1-chome, Tsukuba-shi, Ibaraki, Japan) (ZIP code 305) on Mar. 8, 1996 under the accession number of FERM P-15507 subsequently converted to deposit according to the Budapest Treaty as of Feb. 3, 1997 under the accession number of FERM BP-5810.

The novel cyclic lipopeptide acylase-producing strain named Streptomycessp. No. 6907 (herein after referred to briefly as Strain No. 6907) was isolated for the first time from a soil sample collected in Fukushima Prefecture. The bacteriological characteristics of this Strain No. 6907 are now described.

Cultural Characteristics

The cultural characteristics of Strain No. 6907 on yeast extract-malt extract agar, oatmeal agar, inorganic salts-starch agar, glycerin-asparagine agar, peptone-yeast extract-iron agar, and tyrosine agar after incubation at 30° C. for 14 days and the light and scanning electron microscopic findings of the respective growths are summarized in Table 5.

The color descriptions given below correspond to the nomenclature defined in Methuen Handbook of Colour, Methuen, London, 1978.

TABLE 5

Cultural characteristics of Strain No. 6907

| Medium | Cultural characteristics |
|---|---|
| Yeast extract-malt extract agar (ISP-2) | G: good<br>A: abundant, yellowish gray (white4A2)<br>R: grayish orange (5B6)<br>S: none |
| Oatmeal agar (ISP-3) | G: moderate<br>A: abundant, bluish gray (22C2)<br>R: light brown (4D4)<br>S: none |
| Inorganic salts-starch agar (ISP-4) | G: good<br>A: abundant, bluish gray (19C2)<br>R: brown (6F4)<br>S: none |
| Glycerin-asparagine agar (ISP-5) | G: good<br>A: abundant, bluish gray (22B2)<br>R: reddish brown (8E4)<br>S: none |
| Peptone-yeast extract-iron agar (ISP-6) | G: moderate<br>A: none<br>R: grayish brown (9F3)<br>S: dark brown |
| Tyrosine agar (ISP-7) | G: good<br>A: moderate, yellowish white (4A2)<br>R: dark magenta (13F3)<br>S: dark brown |

Codes: G: growth, A: aerial mycelium, R: reverse side color, S: soluble pigment

The color of the aerial mycelium was yellowish gray to bluish gray, the reverse side color of growth was light brown to brown, and the intracellular pigments were not pH-sensitive. Melanoid pigments were produced in tryptone-yeast extract broth, peptone-yeast extract-iron agar, and tyrosine agar.

Physiological Characteristics

The physiological characteristics of Strain No. 6907 are summarized in Table 6.

TABLE 6

Physiological characteristics of Strain No. 6907

| Parameters | Findings |
|---|---|
| Temperature range for growth | 9.0–40.0° C. |
| Liquefaction of gelatin | + |
| Coagulation of milk | + |
| Peptonization of milk | − |
| Hydrolysis of starch | + |
| production of Melanoid pigments | + |
| Carbon utilization: | |
| D-glucose | + |
| L-arabinose | + |
| D-xylose | + |
| Inositol | + |
| Mannitol | + |
| D-fructose | + |
| L-rhamnose | + |
| Sucrose | + |
| Raffinose | + |

+: positive, ±: weakly positive, −: negative

This strain utilized all the carbon sources tested. It did not peptonize milk. The temperature range for growth was 9.0–40.0° C.

The vegetative mycelium of Strain No. 6907 developed well and branched irregularly but was not fragmented. The aerial mycelium extending from the vegetative mycelium branched monopodially to form elongated spore chains. The spore chain morphology of the aerial mycelium was straight-flexuous or incomplete loops, thus belonging to the RF or RA type according to the classification of Pridham et al. (Pridham, T. G. et al.: Appl. Microbiol., 6:54, 1958). Each spore chain consists of 20 or more spores. The spore is smooth-surface and cylindrical. The spore size is 0.5~0.7× 0.7~1.3 μm. None of sclerotium, sporangium, and zoospore was observed.

Cell Wall Type

As to the cell wall amino acid composition, the whole-cell lysate was analyzed by the method of Becker et al. (Becker, B., M. P. Lechevalier, R. E. Gordon and H. A. Lechevalier: Rapid differentiation between Nocardia and Streptomyces by paper chromatography of whole-cell hydrolysates: Appl. Microbiol., 12:421–423, 1964) and the method of Yamaguchi (Yamaguchi, T.: Comparison of the cell wall composition of morphologically distinct actinomycetes: J. Bacteriol., 89:444–453, 1965). The analysis indicated the existence of LL-diaminopimelic acid. Therefore, the cell wall of this strain was considered to be of Type I.

Based on the above morphological observation and chemical analysis, Strain No. 6907 was considered to belong to the genus Streptomyces according to the taxonomic classification of Pridham et al. (Pridham, T. G. et al: Appl. Microbiol., 6:54, 1958). Accordingly, the characters of this strain were compared with those of Streptomyces species as described in the literature, namely Shirling et al. (Shirling, E. B. and D. Gottlieb: Cooperative Description of Type Culture of Streptomyces. 2. Species descriptions from first study, Intern. J. Syst. Bacteriol., 18:69–189, 1968; Shirling, E. B. and D. Gottlieb: Cooperative Description of Type Culture of Streptomyces. 3. Additional species descriptions from first and second studies, Intern. J. Syst. Bacteriol., 18:279–392, 1968; Shirling, E. B. and D. Gottlieb: Cooperative Description of Type Culture of Streptomyces. 4. Species descriptions from second, third and forth studies, Intern. J. Syst. Bacteriol., 19:391–512, 1969); Skerman et al. (Skerman, V. B., V. McGowan and P. H. A. Sneath: Approved List of Bacterial Names, Amended Edition, American Society for Microbiology, Washington D.C., 1989); and Moore et al. (Moore, W. E., E. P. Cato and L. V. H. Moore: Index of Bacterial and Yeast Nomencultural Changes, American Society for Microbiology, Washington D.C., 1992). The comparison failed to indicate a species to which the strain could be identified and, therefore, this strain was named Streptomyces sp. No. 6907.

This Streptomyces sp. No. 6907 was originally deposited with National Institute of Bioscience and Human Technology (NIBH, 1–3, Higashi 1-chome, Tsukuba-ski, Ibaraki, Japan) (ZIP code 305) on Mar. 8, 1996 under the accession number of FERM P-15506 and subsequently converted to deposit according to the Budapest Treaty as of Feb. 3, 1997 under the accession number of FERM BP-5809.

The term "cyclic lipopeptide compound" as used in this specification means a compound having a polypeptide ring and, on said ring, a side-chain "acylamino" group, optionally with or without one or more other side chains.

Substance FR901379, which is a representative example of said "cyclic lipopeptide compound", is a known antifungal substance produced by the microorganism Coleophoma sp. F-11899 (FERM BP-2635) (described in Japanese Kokai Tokkyo Koho H3-184921) and having the following chemical formula [Ia].

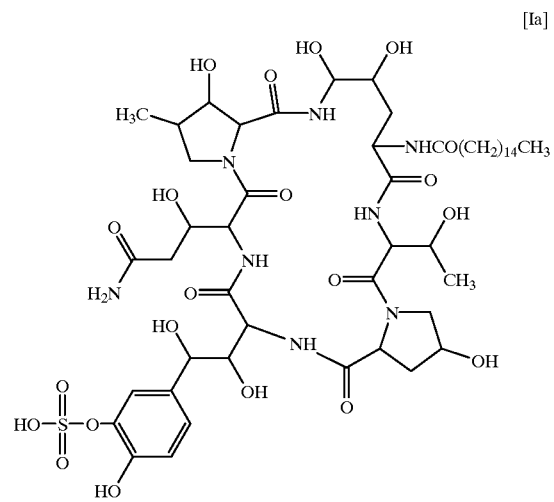

The "Substance FR901379 analog" means a compound of the following general formula [I] or a salt thereof.

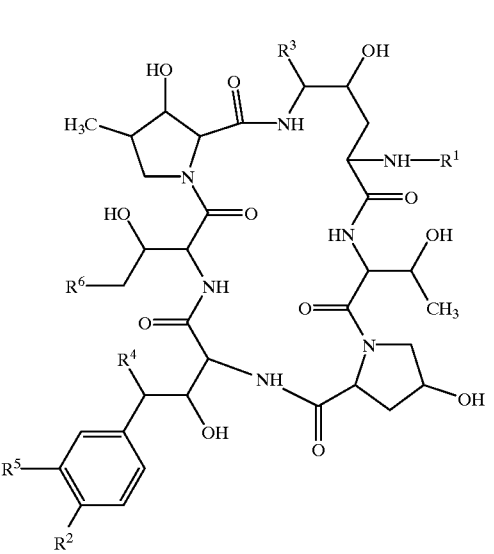

[wherein $R^1$ is acyl, $R^2$ is hydroxy or acyloxy, $R^3$ is hydrogen or hydroxy, $R^4$ is hydrogen or hydroxy, $R^5$ is hydrogen or hydroxysulfonyloxy, and $R^6$ is hydrogen or carbamoyl.]

The novel cyclic lipopeptide acylase of the present invention is an acylase derived from a strain of microorganism of the genus Streptomyces which is capable of deacylating the side chain "acylamino" group of said cyclic lipopeptide compound to an "amino" group. Specifically, it is an acylase which deacylates the palmitoyl side chain of substance FR901379 or a salt thereof or the acyl side chain of said Substance FR901379 analog of general formula [I] or a salt thereof to specifically produce a compound of the following chemical formula [IIa] (Substance FR179642) or a salt thereof.

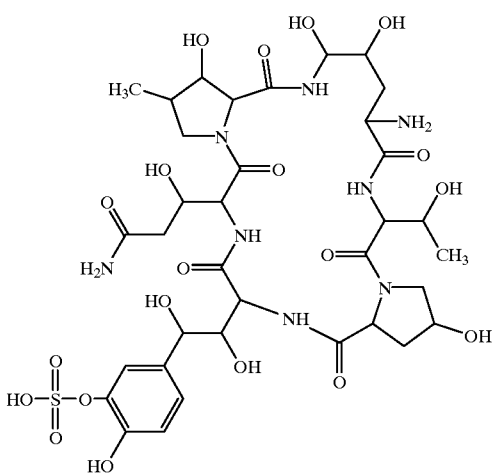

or an FR179642 analog of the following general formula [II], inclusive of Substance FR179642), or a salt thereof.

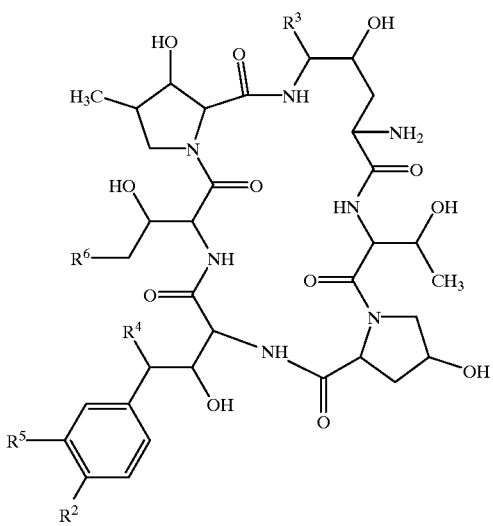

[wherein $R^2$, $R^3$, $R^4$, $R^5$, and $R^6$ are the same groups as respectively defined herein before.]

The preferred salts of compounds [I] and [II] are nontoxic mono- or di-salts of the conventional kinds. Thus, metal salts such as alkali metal salts (e.g. sodium salt, potassium salt, etc.), alkaline earth metal salts (e.g. calcium salt, magnesium salt, etc.), ammonium salt, salts with organic bases (e.g. trimethylamine salt, triethylamine salt, pyridine salt, picoline salt, dicyclohexylamine salt, N,N'-dibenzylethylenediamine salt, etc.), organic acid addition salts (e.g. formate, acetate, trifluoroacetate, maleate, tartarate, methanesulfonate, benzenesulfonate, toluenesulfonate, etc.), inorganic acid addition salts (e.g. hydrochloride, hydrobromide, hydroiodide, sulfate, phosphate, etc.), and salts with amino acids (e.g. arginine, aspartic acid, glutamic acid, etc.) can be mentioned.

The preferred "lower alkyl" is a straight-chain or branched alkyl groups of 1~6 carbon atom(s), such as methyl, ethyl, propyl, isopropyl, butyl, isobutyl, tert-butyl, pentyl, isopentyl, and hexyl. Among them, alkyl groups of 1~4 carbon atom(s) are preferred and methyl is particularly preferred.

The preferred "higher alkyl" includes straight-chain or branched alkyl groups of 7~20 carbon atom(s), such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl, and eicosyl.

The preferred "lower alkoxy" includes straight-chain or branched groups such as methoxy, ethoxy, propoxy, isopropoxy, butoxy, isobutyl, tert-butoxy, pentyloxy, tert-pentyloxy, neo-pentyloxy, hexyloxy, and isohexyloxy.

The preferred "higher alkoxy" includes straight-chain or branched groups such as heptyloxy, octyloxy, 3,5-dimethyloctyloxy, 3,7-dimethyloctyloxy, nonyloxy, decyloxy, undecyloxy, dedecyloxy, tridecyloxy, tetradecyloxy, hexadecyloxy, heptadecyloxy, octadecyloxy nonadecyloxy, and eicosyloxy.

The preferred "aryl" includes phenyl optionally having lower alkyl (e.g. phenyl, mesityl, tolyl, etc.), naphthyl and anthryl, and the like.

The preferred "acyl" moiety in the term of "acylamino" or "acyl" group includes aliphatic acyl, aromatic acyl, heterocyclic acyl, aryl-substituted aliphatic acyl, and heterocyclic-substituted aliphatic acyl derived from carboxylic acids, carbonic acids, carbamic acids, and sulfonic acids.

The preferred "acyl" includes lower alkanoyl (e.g. formyl, acetyl, propionyl, butyryl, isobutyryl, valeryl, hexanoyl, pivaloyl, etc.) which may have one or more (preferably 1~3) suitable substituent(s) such as aryl (e.g. phenyl, naphthyl, anthryl, etc.) which may have one or more (preferably 1~3) suitable substituent(s) such as halogen (e.g. fluoro, chloro, bromo, iodo, etc.), hydroxy, said higher alkoxy, said aryl, etc.; said lower alkoxy; amino; protected amino [preferably acylamino such as lower alkoxycarbonylamino (e.g. methoxycarbonylamino, ethoxycarbonylamino, propoxycarbonylamino, butoxycarbonylamino, tert-butoxycarbonylamino, pentyloxycarbonylamino, hexyloxycarbonylamino, etc.), etc.]; di(lower)alkylamino (e.g. dimethylamino, N-methylethylamino, diethylamino, N-propylbutylamino, dipentylamino, dihexylamino, etc.); lower alkoxyimino (e.g. methoxyimino, ethoxyimino, propoxyimino, butoxyimino, tert-butoxyimino, pentyloxyimino, hexyloxyimino, etc.); ar(lower) alkoxyimino (e.g. benzyloxyimino, phenethyloxyimino, benzhydryloxyimino, etc.) such as phenyl(lower) alkoxyimino which may have one or more (preferably 1~3) suitable substituent(s) such as said higher alkoxy; heterocyclicthio (preferably pyridylthio) which may have one or more (preferably 1~3) suitable substituent(s) such as higher alkyl (e.g. heptyl, octyl, 2-ethylhexyl, nonyl, decyl, 3,7-dimethyloctyl, undecyl, dodecyl, tridecyl, tetradecyl, pentadecyl, 3-methyl-10-ethyldodecyl, hexadecyl, heptadecyl, octadecyl, nonadecyl, eicosyl, etc.); and heterocyclic group (e.g. thienyl, imidazolyl, pyrazolyl, furyl, tetrazolyl, thiazolyl, thiadiazolyl, etc.) which may have one or more (preferably 1~3) suitable substituent(s) such as amino, said protected amino, said higher alkyl, and the like.;

higher alkanoyl (e.g. heptanoyl, octanoyl, nonanoyl, decanoyl, undecanoyl, lauroyl, tridecanoyl, myristoyl, pentadecanoyl, palmitoyl, 10,12-dimethyltetradecanoyl, heptadecanoyl, stearoyl, nonadecanoyl, eicosanoyl, etc.);

lower alkenoyl (e.g. acryloyl, methacryloyl, crotonoyl, 3-pentenoyl, 5-hexenoyl, etc.) which may have one or more (preferably 1~3) suitable substituent(s) such as said aryl optionally having one or more (preferably 1~3) suitable substituent(s) such as said higher alkoxy, etc.;

higher alkenoyl (e.g. 4-heptenoyl, 3-octenoyl, 3,6-decadienoyl, 3,7,11-trimethyl-2,6,10-dodecatrienoyl, 4,10-heptadecadienoyl, etc.);

lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.);

higher alkoxycarbonyl (e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexdecyloxycarbonyl, heptadecyloxycarbonyl, octadecyloxycarbonyl, nonadecyloxycarbonyl, eicosyloxycarbonyl, etc.);

aryloxycarbonyl (e.g. phenoxycarbonyl, naphthyloxycarbonyl, etc.);

arylglyoxyloyl (e.g. phenylglyoxyloyl, naphthylglyoxyloyl, etc.);

ar(lower)alkoxycarbonyl which may have one or more suitable substituent(s), for example phenyl(lower) alkoxycarbonyl which may have nitro or lower alkoxy (e.g. benzyloxycarbonyl, phenethyloxycarbonyl, p-nitrobenzyloxycarbonyl, p-methoxybenzyloxycarbonyl, etc.);

lower alkylsulfonyl (e.g. methylsulfonyl, ethylsulfonyl, propylsulfonyl, isopropylsulfonyl, pentylsulfonyl, butylsulfonyl, etc.);

arylsulfonyl (e.g. phenylsulfonyl, naphthylsulfonyl, etc.) which may have one or more (preferably 1~3) suitable substituent(s) such as said lower alkyl, said higher alkoxy, and the like;

ar(lower)alkylsulfonyl (e.g. benzylsulfonyl, phenethylsulfonyl, benzhydrylsulfonyl, etc.), for example phenyl (lower)alkylsulfonyl; and aroyl (e.g. benzoyl, naphthoyl, anthrylcarbonyl, etc.) which may have one or more (preferably 1~5) suitable substituent(s) such as said halogen; lower alkyl (e.g. methyl, ethyl, propyl, butyl, tert-butyl, pentyl, hexyl, etc.); said higher alkyl; lower alkoxy (e.g. methoxy, ethoxy, propoxy, butoxy, tert-butoxy, pentyloxy, hexyloxy, etc.) which may have one or more (preferably 1~10) suitable substituent(s) such as said lower alkoxy, said halogen, said aryl, and the like; higher alkoxy (e.g. heptyloxy, octyloxy, 2-ethylhexyloxy, nonyloxy, decyloxy, 3,7-dimethyloctyloxy, undecyloxy, dodecyloxy, tridecyloxy, tetradecyloxy, pentadecyloxy, 3-methyl-10-ethyldodecyloxy, hexadecyloxy, heptadecyloxy, octadecyloxy, nonadecyloxy, eicosyloxy, etc.) which may have one or more (preferably 1~17) suitable substituent(s) such as said halogen, and the like; higher alkenyloxy (e.g. 3-heptenyloxy, 7-octenyloxy, 2,6-octadienyloxy, 5-nonenyloxy, 1-decenyloxy, 3,7-dimethyl-6-octenyloxy, 3,7-dimethyl-2,6-octadienyloxy, 8-undecenyloxy, 3,6,8-dodecatrienyloxy, 5-tridecenyloxy, 7-tetradecenyloxy, 1,8-pentadecadienyloxy, 15-hexadecenyloxy, 11-heptadecenyloxy, 7-octadecenyloxy, 10-nonadecenyloxy, 18-eicosenyloxy, etc.); carboxy; said aryl which may have one or more (preferably 1~3) suitable substituent(s) such as said higher alkoxy and the like; and aryloxy (e.g. phenoxy, naphthyloxy, anthryloxy, etc.) which may have one or more (preferably 1~3) suitable substituent (s) such as said lower alkoxy and said higher alkoxy.

Among the above examples of "acyl", higher alkanoyl group is preferred and palmitoyl is particularly preferred.

The preferred "acyl" moiety in the term of "acyloxy" can be referred to aforementioned "acyl" group.

The preferred "acyloxy" group includes lower alkanoyloxy (e.g. formyloxy, acetyloxy, propionyloxy, butyryloxy, isobutyryloxy, valeryloxy, hexanoyloxy, pivaloyloxy, etc.) or phosphonoxy.

The novel cyclic lipopeptide acylase of the invention can be produced by growing an acylase-producing strain of microorganism belonging to the genus Streptomyces, such as *Streptomyces anulatus* No. 4811 (FERM BP-5808), *Streptomyces anulatus* No. 8703 (FERM BP-5810), or Streptomyces sp. No. 6907 (FERM BP-5809), in a culture medium.

Generally, this novel acylase can be produced by growing said novel acylase-producing strain of microorganism in an aqueous medium containing assimilable carbon and digestable nitrogen sources preferably under aerobic conditions, for example by shake culture and submerged culture.

The preferred carbon source for the medium includes various carbohydrates such as glucose, xylose, galactose, glycerin, starch, dextrin, and the like. As other carbon sources, maltose, rhamnose, raffinose, arabinose, mannose, salicin, sodium succinate, and the like can be mentioned.

The preferred nitrogen source includes yeast extract, peptone, gluten meal, cottonseed flour, soybean flour, corn steep liquor, dried yeast, wheat germs, down meal, peanut flour, and the like. as well as inorganic or organic nitrogenous compounds such as ammonium salts, (e.g. ammonium nitrate, ammonium sulfate, ammonium phosphate, etc.), urea, and amino acids.

While those carbon and nitrogen sources are used preferably in suitable combinations, even materials of low purity can be used provided that they contain suitable amounts of growth factors and reasonable amounts of inorganic nutrients and it is not always necessary to use them in the pure form. Optionally, the medium may be supplemented with sodium carbonate or potassium carbonate, sodium phosphate or potassium phosphate, sodium chloride or potassium chloride, sodium iodide or potassium iodide, and inorganic salts such as magnesium salts, copper salts and cobalt salts. Particularly, when the culture medium produces a copious foam, a deforming agent such as liquid paraffin, fatty oil, vegetable oil, mineral oil, and silicone may be added as necessary.

For the mass production of the novel acylase, the submerged aerobic cultural method is preferred. For minor-scale production, shake culture or surface culture is carried out in a flask or bottle. For large-capacity tank culture, the fermentation tank is preferably inoculated with a seed culture for avoiding a delay in growth in the production line for the novel acylase. Thus, preferably a comparatively small amount of culture medium is first inoculated with the spores or mycelium of the strain and incubated to prepare a seed culture which is then aseptically transferred to a large-capacity fermentation tank. The medium for this seed culture may be substantially the same as production medium for the novel acylase or different from the production medium.

The agitation and aeration of the fermentation system can be carried out in various ways. For example, the agitation can be effected by using a propeller or other similar stirring device, rotating or shaking the fermentator, by means of a pump of choice, or passing sterile air through the medium. The aeration can be achieved by blowing sterile air into the fermentation system.

The fermentation is carried out generally within the temperature range of about 20~32° C., preferably 25~30° C., and the pH range of 6~8 for about 50~150 hours. Those conditions may be modified according to other cultural conditions and fermentation scale.

The novel acylase thus produced can be recovered from the fermentation broth by techniques which are routinely used for recovery of other known bioactive substances. The novel acylase elaborated is found in both the grown mycelium and the filtrate. Therefore, the novel acylase can be separated from the mycelial cake and filtrate available upon filtration or centrifugation of the broth and purified by the conventional methods such as concentration under reduced pressure, freeze-drying, extraction with the common solvent, pH adjustment, treatment with a conventional resin, (e.g. anion exchange resin, cation exchange resin, nonionic adsorbent resin, etc.), treatment with an ordinary adsorbent such as active charcoal, silicic acid, silica gel, cellulose, alumina, crystallization, and recrystallization.

The following examples illustrate the acylase produced by *Streptomyces anulatus* No. 4811, *Streptomyces anulatus* No. 8703, or Streptomyces sp. No. 6907 in further detail and should by no means be construed as defining the scope of the invention.

EXAMPLE 1-1

Production of the acylase of the *Streptomyces anulatus* No. 4811 origin

A conical flask of 100-ml capacity was charged with 30 ml of a seed culture medium containing 1% of corn starch, 1% of glucose, 0.5% of peanut flour, 0.5% of soybean flour, 0.5% of dried yeast, and 0.2% of calcium carbonate and sterilized at 120° C. for 20 minutes. The sterilized flask was then inoculated with 1~2 loopful(s) of a slant agar culture of *Streptomyces Anulatus* No. 4811 and incubated under shaking at 30° C. for 3 days to provide a seed culture.

Meanwhile, a production medium containing 4% of sucrose, 1% of peanut flour, 1% of dried yeast, 0.05% of potassium dihydrogen phosphate, 0.12% of dipotassium hydrogen phosphate, and 0.025% of magnesium sulfate 7H$_2$O was adjusted to pH 6.5 and a conical flask of 500-ml capacity was filled with 100 ml of the production medium and sterilized at 120° C. for 20 minutes. The sterilized flask was inoculated with 2 ml of the above seed culture and incubated under shaking at 30° C. for 3 days to provide a fermentation broth.

EXAMPLE 1-2

Production of the acylase of the *Streptomyces anulatus* No. 8703 origin

A conical flask of 100-ml capacity was charged with 30 ml of a seed culture medium containing 1% of corn starch, 1% of glucose, 0.5% of peanut flour, 0.5% of soybean flour, 0.5% of dried yeast, and 0.2% of calcium carbonate and sterilized at 120° C. for 20 minutes. The sterilized flask was then inoculated with 1~2 loopful(s) of a slant agar culture of *Streptomyces anulatus* No. 8703 and incubated under shaking at 30° C. for 3 days to provide a seed culture.

Meanwhile, a production medium containing 4% of sucrose, 1% of peanut flour, 1% of dried yeast, 0.05% of potassium dihydrogen phosphate, 0.12% of dipotassium hydrogen phosphate, and 0.025% of magnesium sulfate 7H$_2$O was adjusted to pH 6.5 and a conical flask of 500-ml capacity was filled with 100 ml of the production medium and sterilized at 120° C. for 20 minutes. The sterilized flask was inoculated with 2 ml of the above seed culture and incubated under shaking at 30° C. for 3 days to provide a fermentation broth.

EXAMPLE 1-3

Production of the acylase of the Streptomyces sp. No. 6907 origin

A conical flask of 100-ml capacity was charged with 30 ml of a seed medium containing 6% of soluble starch, 4% of defatted soybean meal, and 0.5% of calcium carbonate and sterilized at 120° C. for 20 minutes. The sterilized flask was then inoculated with 1~2 loopful(s) of a slant agar culture of Streptomyces sp. No. 6907 and incubated under shaking at 30° C. for 3 days to provide a seed culture.

Meanwhile, a production medium containing 4% of sucrose, 1% of peanut flour, 1% of dried yeast, and 0.5% of calcium carbonate was adjusted to pH 6.5 and a conical flask of 500-ml capacity was charged with 100 ml of the production medium and sterilized at 120° C. for 20 minutes. The sterilized flask was inoculated with 2 ml of the above seed culture and incubated under shaking at 30° C. for 2 days to provide a fermentation broth.

EXAMPLE 1-4

Production of the acylase of the allotted Streptomyces origin

Using the following Streptomyces strain allotted from Institute for Fermentation, Osaka (IFO, Feb. 17, 1985, Juso Hommachi, Yodogawa-ku, Osaka-shi), the cultivation procedure of Example 1-1 for *Streptomyces anulatus* No. 4811 was otherwise repeated to provide a fermentation broth.

*Streptomyces griseus* subsp. *griseus* IFO 13189

The method of deacylating the acyl side chain of the antifungal cyclic lipopeptide compound (e.g. FR901379 or its analog) with the novel cyclic lipopeptide acylase of the invention is now described in detail.

The deacylation method of the invention can be carried out in the following manner.

A suitable production medium is inoculated with a strain of microorganism belong to the genus Streptomyces and capable of producing the novel acylase and the inoculated medium was incubated at about 25~35° C. for a few days to provide a fermentation broth. This fermentation broth is added to the substrate cyclic lipopeptide compound, such as Substance FR901379, and the mixture is incubated at 45~60° C. and pH about 6.0~9. Then, the cyclic peptide such as Substance FR179642 is detected and separated by high-performance liquid chromatography (HPLC).

The following examples are intended to illustrate the deacylation method of the invention in detail and should by no means be construed as defining the scope of the invention.

EXAMPLE 2-1

To 700 μl of the fermentation broth of *Streptomyces anulatus* No. 4811 obtained in Example 1-1 was added 100 μl of an aqueous solution of Substance FR901379 (100 mg/ml) (10 mg as Substance FR901379; 8.35 μmol) together with 100 μl of methanol and 100 μl of buffer (0.5 M potassium dihydrogen phosphate-disodium hydrogen phosphate buffer; pH 6.0), and the reaction was carried out at 30° C. for 30 minutes. The reaction was then stopped with 1 ml of 4% acetic acid and following addition of 2 ml of methanol, the mixture was filtered through a membrane filter (0.45 μm) to remove the macromolecular protein and other fraction and subjected to HPLC and the acylase activity of the skeletal substance FR179642 produced was monitored and assayed at 210 nm.

Using a variable wavelength UV detected (Shimadzu SPD-10A), a pump (Shimadzu LC-10AD) and an integrator (Shimadzu C-R6A) as the instrumentation, LiChrospher 100RP-18(e) (250 mm×4 mm i.d., particle diameter 5 μm (E. Merck)) as the stationary phase, and 3% acetonitrile/0.5% ammonium dihydrogen phosphate as the mobile phase, Substance FR179642 was eluted at a flow rate of 1 ml/min. The retention time of Substance FR179642 was about 6.3 minutes. The yield of Substance FR179642 as calculated from HPLC data was 730 μg (0.78 μmol).

EXAMPLE 2-2

To 700 µl of the fermentation broth of *Streptomyces anulatus* No. 8703 obtained in Example 1-2 was added 100 µl of an aqueous solution of Substance FR901379 (100 mg/ml) (10 mg as Substance FR901379; 8.35 µmol) together with 100 µl of methanol and 100 µl of buffer (0.5 M potassium dihydrogen phosphate-disodium hydrogen phosphate buffer; pH 6.0), and the reaction was carried out at 30° C. for 30 minutes. The reaction was then stopped with 1 ml of 4% acetic acid and following addition of 2 ml of methanol, the mixture was filtered through a membrane filter (0.45 µm) to remove the macromolecular protein and other fraction and subjected to HPLC and the acylase activity of the skeletal substance FR179642 produced was monitored and assayed at 210 nm.

Using a variable wavelength UV detector (Shimadzu SPD-10A), a pump (Shimadzu LC-10AD) and an integrator (Shimadzu C-R6A) as the instrumentation, LiChrospher 100RP-18(e) (250 mm×4 mm i.d., particle diameter 5 µm (E. Merck)) as the stationary phase, and 3% acetonitrile/0.5% ammonium dihydrogen phosphate as the mobile phase, Substance FR179642 was eluted at a flow rate of 1 ml/min. The retention time of Substance FR179642 was about 6.3 minutes. The yield of Substance FR179642 as calculated from HPLC data was 830 µg (0.89 µmol).

EXAMPLE 2-3

To 700 µl of the fermentation broth of Streptomyces sp. No. 6907 obtained in Example 1-3 was added 100 µl of an aqueous solution of Substance FR901379 (100 mg/ml) (10 mg as Substance FR901379; 8.35 µmol) together with 100 µl of methanol and 100 µl of buffer (0.5 M potassium dihydrogen phosphate-disodium hydrogen phosphate buffer; pH 6.0), and the reaction was carried out at 30° C. for 30 minutes. The reaction was then stopped with 4% acetic acid and following addition of 2 ml of methanol, the mixture was filtered through a membrane filter (0.45 µm) to remove the macromolecular protein and other fraction and subjected to HPLC and the acylase activity of the skeletal substance FR179642 produced was monitored and assayed at 210 nm.

Using a variable wavelength UV detector (Shimadzu SPD-10A), a pump (Shimadzu LC-10AD) and an integrator (Shimadzu C-R6A) as the instrumentation, LiChrospher 100RP-18(e) (250 mm×4 mm i.d., particle diameter 5 µm (E. Merck)) as the stationary phase, and 3% acetonitrile/0.5% ammonium dihydrogen phosphate as the mobile phase, Substance FR179642 was eluted at a flow rate of 1 ml/min. The retention tie of Substance FR179642 was about 6.3 minutes. The yield of Substance FR179642 as calculated from HPLC data was 560 µg (0.60 µmol). The Km value determined by the Lineweaver-Burk method was 257 µM and Vmax was 14.3 U/mg-protein.

EXAMPLE 2-4

To 100 µl of the fermentation broth of Streptomyces sp. No. 6907 obtained in Example 1-3 was added 100 µl of a dimethyl sulfoxide solution of Aculeacin A (100 mg/ml) (10 mg as Aculeacin A; 9.65 µmol) together with 500 µl of 1.2 M KCl-containing 500 mM potassium dihydrogen phosphate-disodium hydrogen phosphate buffer (pH 7.0) and 300 µl of water, and the reaction was carried out at 40° C. for 15 minutes. The reaction was then stopped with 1 ml of 4% acetic acid and following addition of 2 ml of methanol, the mixture was filtered through a membrane filter (0.45 µm) to remove the macromolecular protein and other fraction and subjected to HPLC and the acylase activity of the nuclear substance Aculeacin A produced was monitored at 210 nm and determined. Using a variable wavelength UV detector (Shimadzu SPD-10A), a pump (Shimadzu LC-10AD) and an integrator (Shimadzu C-R6A) as the instrumentation, LiChrospher 100RP-18(e) (250 mm×4 mm i.d., particle diameter 5 µm (E. Merck)) as the stationary phase, and 4% acetonitrile/1% ammonium dihydrogen phosphate as the mobile phase, nuclear substance Aculeacin A was eluted at a flow rate of 1 ml/min. The retention time of nuclear substance Aculeacin A was about 8.7 minutes. The yield of nuclear substance Aculeacin A as calculated from HPLC data was 370 µg (0.47 µmol). The Km value determined by the Lineweaver-Burk method was 279 µM and Vmax was 16.8 U/mg-protein.

EXAMPLE 2-5

To 100 µl of the fermentation broth of Streptomyces sp. No. 6907 obtained in Example 1-3 was added 100 µl of a dimethyl sulfoxide solution of Echinocandin B (100 mg/ml) (10 mg as Echinocandin B; 9.43 µmol) together with 500 µl of 1.2 M KCl-containing 500 mM potassium dihydrogen phosphate-disodium hydrogen phosphate buffer (pH 7.0) and 300 µl of water, and the reaction was carried out at 40° C. for 15 minutes. The reaction was then stopped with 1 ml of 4% acetic acid and following addition of 2 ml of methanol, the mixture was filtered through a membrane filter (0.45 µm) to remove the macromolecular protein and other fraction and subjected to HPLC and the acylase activity of the nuclear substance Echinocandin B produced was monitored and assayed at 210 nm. Using a variable wavelength UV detector (Shimadzu SPD-10A), a pump (Shimadzu LC-10AD) and an integrator (Shimadzu C-R6A) as the instrumentation, LiChrospher 100RP-18(e) (250 mm×4 mm i.d., particle diameter 5 µm (E. Merck)) as the stationary phase, and 4% acetonitrile/1% ammonium dihydrogen phosphate as the mobile phase, nuclear substance Echinocandin B was eluted at a flow rate of 1 ml/min. The retention time of nuclear substance Echinocandin B was about 8.7 minutes. The yield of nuclear substance Echinocandin B as calculated from HPLC data was 90 µg (0.11 µmol). The Km value determined by the Lineweaver-Burk method was 146 µM and Vmax was 7.85 U/mg-protein.

The following characterizes the process of deacylation of the acyl side chain of an antifungal cyclic lipopeptide compound (e.g. Substance FR901379) by the acylase derived from the novel acylase-producing strain of microorganism belong to the genus Streptomyces in accordance with the present invention.

The data shown were generated by the experimental method described in Example 2-1, Example 2-2, or Example 2-3 but varying the kind of buffer (0.5 M sodium citrate buffer, 0.5 M potassium dihydrogen phosphate-disodium hydrogen phosphate buffer, and Tris-HCl buffer were used in various combinations), reaction temperature, and addition level of methanol. Each acylase activity is shown in the concentration (measured by HPLC) of Substance FR179642 at completion of the reaction.

Optimal Reaction pH

Test 1-1

Optimal pH for the acylase produced by *Streptomyces anulatus* No. 4811

| pH | Concentration of Substance FR179642 at completion of reaction (μg/ml) |
|---|---|
| 3 | 0 |
| 4 | 90 |
| 5 | 440 |
| 6 | 630 |
| 6.5 | 710 |
| 7 | 770 |
| 8 | 810 |
| 9 | 740 |

Test 1-2

Optical pH for the acylase produced by *Streptomyces anulatus* No. 8703

| pH | Concentration of Substance FR179642 at completion of reaction (μg/ml) |
|---|---|
| 3 | 0 |
| 4 | 240 |
| 5 | 590 |
| 6 | 810 |
| 7 | 1,070 |
| 8 | 1,300 |
| 9 | 1,270 |

Test 1-3

Optimal pH for the acylase produced by Streptomyces sp. No. 6907

| pH | Concentration of Substance FR179642 at completion of reaction (μg/ml) |
|---|---|
| 3 | 0 |
| 4 | 190 |
| 5 | 280 |
| 6 | 300 |
| 7 | 470 |
| 8 | 800 |
| 9 | 1,000 |

The above results indicate that, in the working of the invention with any of the above acylases, the reaction proceeds at and over weak acidity (pH about 4) and that the reaction rate is increased as the pH is enhanced.

Optimal Reaction Temperature

Test 2-1

Optimal temperature for the acylase produced by *Streptomyces anulatus* No. 4811

| Temperature | Concentration of Substance FR179642 at completion of reaction (μg/ml) |
|---|---|
| 25 | 360 |
| 30 | 630 |
| 40 | 1,490 |
| 50 | 3,120 |
| 60 | 1,110 |
| 70 | 60 |

Test 2-2

Optimal temperature for the acylase produced by *Streptomyces anulatus* No. 8703

| Temperature | Concentration of Substance FR179642 at completion of reaction (μg/ml) |
|---|---|
| 25 | 410 |
| 30 | 770 |
| 40 | 1,760 |
| 50 | 3,160 |
| 60 | 2,110 |
| 70 | 120 |

Test 2-3

Optimal temperature for the acylase produced by Streptomyces sp. No. 6907

| Temperature | Concentration of Substance FR179642 at completion of reaction (μg/ml) |
|---|---|
| 25 | 600 |
| 30 | 710 |
| 40 | 3,010 |
| 50 | 4,620 |
| 60 | 1,660 |
| 70 | 130 |

The above results indicate that, in the working of the invention with any of the above acylases, the optimal reaction temperature is 40~60° C.

Effect of Methanol Added to the Reaction System

Test Example 3-1

The effect of methanol of the reaction using the acylase produced by *Streptomyces anulatus* No. 4811

| Concentration of methanol (%) | Concentration of Substance FR179642 at completion of reaction (μg/ml) |
|---|---|
| 0 | 390 |
| 5 | 570 |
| 10 | 630 |
| 15 | 590 |
| 20 | 550 |
| 30 | 390 |
| 40 | 130 |
| 50 | 10 |

Test 3-2

The effect of methanol on the reaction using the acylase produced by *Streptomyces anulatus* No. 8703

| Concentration of methanol (%) | Concentration of Substance FR179642 at completion of reaction (μg/ml) |
|---|---|
| 0 | 320 |
| 5 | 580 |
| 10 | 770 |
| 15 | 750 |
| 20 | 660 |
| 30 | 360 |
| 40 | 140 |
| 50 | 50 |

Test 3-3

The effect of methanol on the reaction using the acylase produced by Streptomyces sp. No. 6907

| Concentration of methanol (%) | Concentration of Substance FR179642 at completion of reaction (μg/ml) |
|---|---|
| 0 | 330 |
| 5 | 580 |
| 10 | 710 |
| 15 | 630 |
| 20 | 530 |
| 30 | 140 |
| 40 | 130 |
| 50 | 90 |

The above results indicate that, in the working of the invention with any of the above acylases, the activity is increased 1.6-fold through 2.2-fold in the presence of 5~20% of methanol.

The cyclic lipopeptide acylase obtained by growing an acylase-producing strain of microorganism of the genus Streptomyces is now described in detail.

Characteristics of the acylase produced by Streptomyces sp. 6907

1) Activity

This enzyme catalyzes the deacylation of the lipid acyl moiety of the cyclic lipopeptide compound represented by Substance FR901379 and FR901379 analogs such as Echinocandin B and Aculeacin A.

2) Optimal pH: pH 8~9

3) Optimal temperature for activity: about 50° C.

4) Inhibition, activation, and stabilization

Methanol: The enzyme is activated concentration-dependently up to 10% in the reaction mixture and is inhibited at higher concentration.

5) Molecular weight

SDS-PAGE of the purified enzyme gave two bands.

Large peptide: 61 kD

Small peptide: 19 kD

6) Crystal structure

The purified protein was small in amount and not crystalline.

7) Amino acid analysis

N-terminal amino acid sequences

Large peptide SEQ ID NO:1:

Ser-Asn-Ala-Val-Ala-Phe-Asp-Gly-Ser-Thr-Thr-Val-Asn-Gly-Arg-Gly-Leu-Leu-Leu-Gly- . . . .

Small peptide: SEQ ID NO:2:

Gly-Ser-Gly-Leu-Ser-Ala-Val-Ile-Arg-Tyr-Thr-Glu-Tyr-Gly-Ile-Pro-His-Ile-Val-Ala- . . . .

8) Substrate specificity

The enzyme acts as a catalyst for FR901379, Echinocandin B and Aculeacin A. However, it does not act upon FR901469.

The following examples illustrate the acylase of the invention in further detail but should by no means be construed as defining the scope of the invention.

Purification of the acylase

EXAMPLE 3

The fermentation broth of Streptomyces sp. No. 6907 obtained in example 1-3was extracted with 1.5 M KCl under stirring at a low temperature and the filtrate separated with No. 2 filter paper was desalted with an UF membrane (Asahi Chemical Industries; AIP-1010) [20 mm Tris-HCl buffer (pH 9) substituted] and passed through an HP-20 column. The effluent was applied to a DEAE-Toyopearl column (Cl⁻-form) and elution was carried out with 0.3 M NaCl-supplemented 20 mM Tris-HCl buffer (pH 9). In the resulting active fraction, a 0.5 M equivalent of $(NH_4)_2SO_4$ was dissolved, and the solution was applied to a phenyl-Toyopearl column, elution being then carried out with 0.1 M NaCl-supplemented 50 mM Tris-HCl buffer (pH 8). The resulting active fraction was desalted and concentrated with a DF membrane (Asahi Chemical Industries; SIP-0013) [20 mM Tris-HCl buffer (pH 9) substituted] and subjected to gel permeation chromatography on a YMC-Diol column (mobile phase: 0.2 M NaCl-0.1 M potassium dihydrogen phosphate-disodium hydrogen phosphate buffer pH 7.0). The active fraction was further purified by preparative chromatography on a reversed phase Cosmosil 5C4-AR-300 column [mobile phase: (A solution) 0.5% trifluoroacetic acid, (B solution) 0.5% trifluoroacetic acid—80% acetonitrile, A:B=60:40→40:60 (linear gradient)], whereby two bands were obtained. The thus-purified acylase was subjected to SDS-PAGE in this manner, two different peptides having molecular masses of 61 kD and 19 kD, respectively, were provided.

Substrate specificity

Substance FR901469 is a known substance (described in WO 92/19648) having antifungal activity as produced by the fungal strain No. 11243 (FERM BP-3373). It is a compound of the following chemical formula [III]:

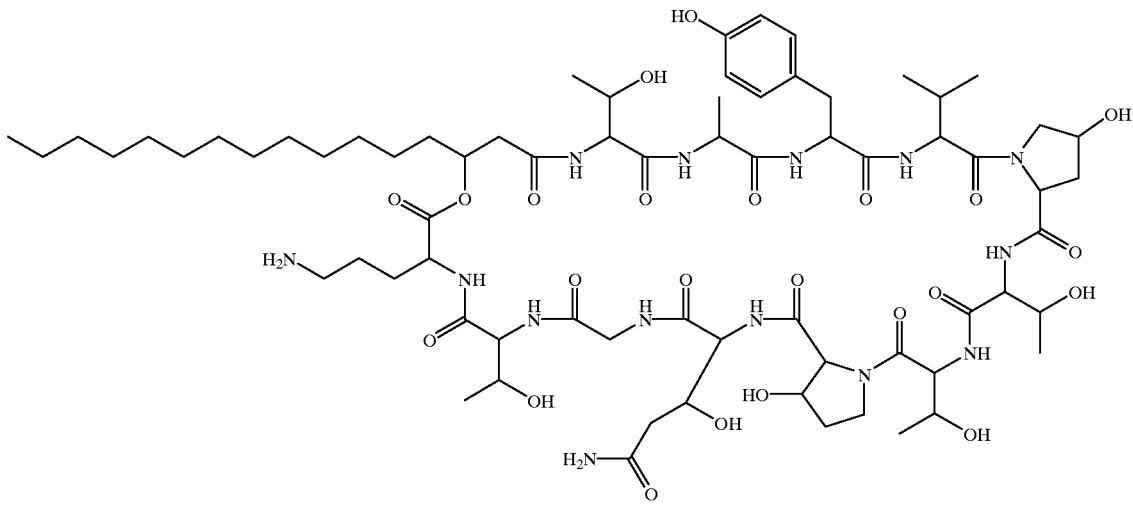

The *Actinoplanes utahensis*-derived acylase (described in Japanese Kokai Tokkyo Koho H4-228072), which has deacylation activity as does the novel acylase according to the present invention, exerts a catalytic action on said Substance FR901469 and its salt to produce Substance FR181131 (described in WO 96/30399) of the following chemical formula [IV]:

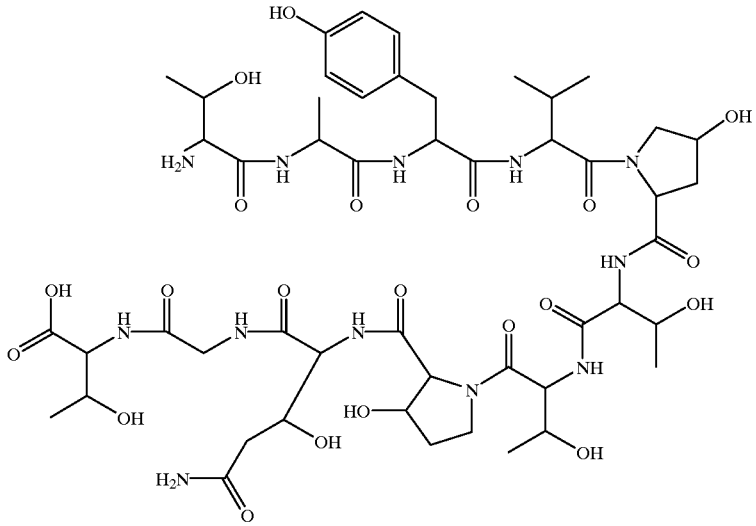

In contrast, the novel acylase of the present invention exerts no catalytic action on said Substance FR901469 and its salt.

Examples of the invention are presented below.

EXAMPLE 4-1

To 20 ml of a fermentation broth of *Actinoplanes utahensis* IFO13244 as prepared by the procedure described in J. Antibiotics, Vol. 41, p. 1085–1092 ('88) was added 1 ml of an aqueous solution of Substance FR901469 (200 mg/ml) (0.2 g as Substance FR901469; 130 μmol) together with 2.9 g of disodium hydrogen phosphate and 60 ml of water, and the reaction was carried out at 60° C. for 24 hours. After completion of the reaction, the reaction mixture was filtered through a membrane filter (0.45 μm) to remove the high molecular protein and other fraction and purified by HPLC under monitoring for Substance FR181131 at 210 nm and the acylase activity was determined. Using a variable wavelength UV detector (Shimadzu SPD-10A), a pump (Shimadzu LC-10AD) and an integrator (Shimadzu C-R6A) as the instrumentation, YMC AM303 (250 mm×4 mm i.d., particle diameter 5 μm) as the stationary phase, and 12.5% acetonitrile/0.5% ammonium dihydrogen phosphate as the mobile phase, Substance FR181131 was eluted at a flow rate of 1 ml/min. The retention time of Substance FR181131 was about 7.3 minutes. The yield of Substance FR181131 as calculated from HPLC data was 80 mg (68 μmol).

EXAMPLE 4-2

To 20 ml of the fermentation broth of Streptomyces sp. No. 6907 obtained in Example 1-3 was added 1 ml of an aqueous solution of Substance FR901469 (200 mg/ml) (0.2 g as Substance FR901469; 130 μmol) together with 2.9 g of disodium hydrogen phosphate and 60 ml of water, and the reaction was carried out at 60° C. for 24 hours. After completion of the reaction, the reaction mixture was filtered through a membrane filter (0.45 μm) to remove the high molecular protein and other fraction and purified by HPLC under monitoring for Substance FR181131 at 210 nm and the acylase activity was determined. Using a variable wavelength UV detector (Shimadzu SPD-10A), a pump (Shimadzu LC-10AD) and an integrator (Shimadzu C-R6A) as the instrumentation, YMC AM303 (250 mm×4 mm i.d., particle diameter 5 μm) as the stationary phase, and 12.5% acetonitrile/0.5% ammonium dihydrogen phosphate as the mobile phase, Substance FR181131 was eluted at a flow rate of 1 ml/min. The retention time of Substance FR181131 was about 7.3 minutes. The yield of Substance FR181131 as calculated from HPLC data was not over 2 mg (1.7 μmol) (below detection limit).

Coleophoma sp. F-11899, which produces Substance FR901379, and *Streptomyces anulatus* No. 4811, *Streptomyces anulatus* No. 8703, and Streptomyces sp. No. 6907, all of which produce the acylase of the invention, have all been deposited with National Institute of Bioscience and Human Technology (NIBH, 1–3, Higashi 1-chome, Tsukuba-shi, Ibaraki, Japan).

| Microorganism | Accession No. |
| --- | --- |
| Coleophoma sp. F-11899 | FERM BP-2635 |
| *Streptomyces anulatus* No. 4811 | FERM BP-5808 |
| *Streptomyces anulatus* No. 8703 | FERM BP-5810 |
| Streptomyces sp. No. 6907 | FERM BP-5809 |
| Strain No. 11243 | FERM BP-3373 |

What is claimed is:

1. An isolated acylase enzyme obtained from *Streptomyces anulatus* No. 4811 or *Streptomyces anulatus* No. 8703, wherein said enzyme catalyzes deacylation of the acyl group $R^1$ of a cyclic lipopeptide compound of the following general formula I or a salt thereof:

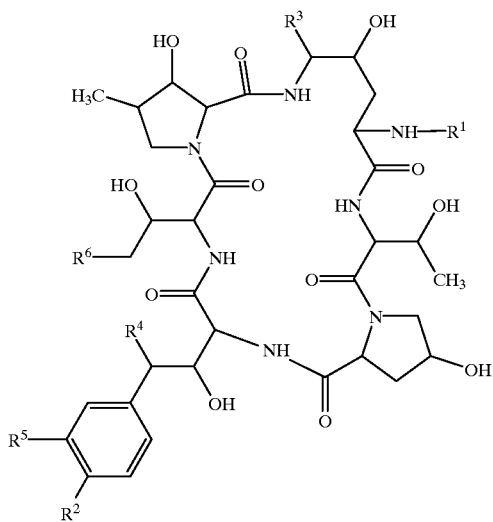

wherein
R¹ is acyl;
R² is hydroxy or acyloxy;
R³ is hydrogen or hydroxy;
R⁴ is hydrogen or hydroxy;
R⁵ is hydrogen or hydroxysulfonyloxy; and
R⁶ is hydrogen or carbamoyl;
to produce a cyclic peptide compound of the following general formula [II] or a salt thereof:

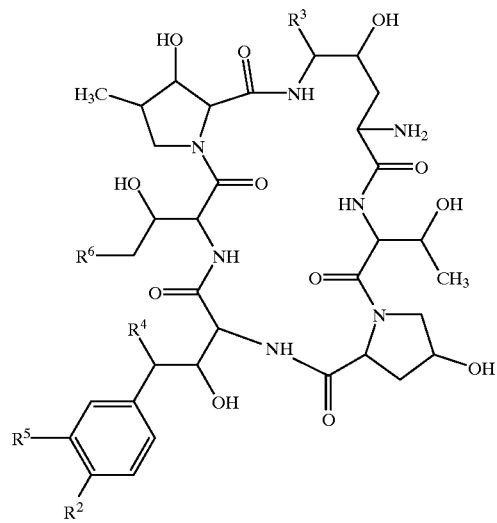

wherein R², R³, R⁴, R⁵, and R⁶ are as defined above; wherein said enzyme deacylates at an optimal pH of 8.0, at an optimal temperature of 50° C., and is activated in a concentration-dependent manner by methanol, wherein activation increases up to 10% by volume concentration of methanol, wherein the enzyme does not deacylate the compound FR901469.

2. The enzyme of claim 1, wherein said cyclic lipopeptide compound is selected from the group consisting of FR901379, Echinocandin B, and Aculeacin A.

3. An isolated enzyme obtained from Streptomyces No. 6907, comprising a large peptide and a small peptide wherein said large peptide comprises SEQ ID NO:1 and said small peptide comprises SEQ ID NO:2, wherein said enzyme catalyzes the deacylation of the lipid acyl moiety of a cyclic lipopeptide at an optimal pH of 9.0, an optimal temperature of 50° C., and is activated in a concentration-dependent manner by methanol, wherein activation increases up to 10% by volume concentration of methanol, and wherein the enzyme does not deacylate the compound FR901469.

4. The enzyme of claim 3, wherein said large peptide is approximately 61 kD and said small peptide is approximately 19 kD as determined by SDS-PAGE.

5. The enzyme of claim 3, wherein the enzyme deacylates a compound selected from the group consisting of FR901379, Echinocandin B, and Aculeacin A.

6. The acylase of claim 3 which catalyzes deacylation of the acyl group R¹ of a cyclic lipopeptide compound of the following general formula I or a salt thereof:

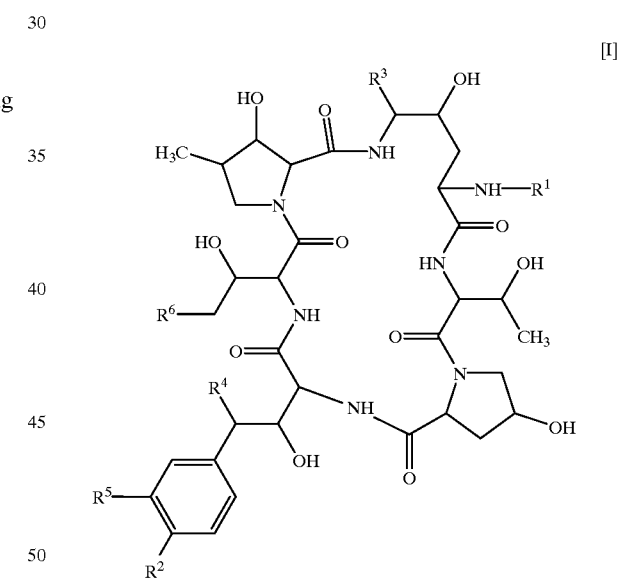

wherein
R¹ is acyl;
R² is hydroxy or acyloxy;
R³ is hydrogen or hydroxy;
R⁴ is hydrogen or hydroxy;
R⁵ is hydrogen or hydroxysulfonyloxy; and
R⁶ is hydrogen or carbamoyl;
to produce a cyclic peptide compound of the following general formula [II] or a salt thereof:

[II]

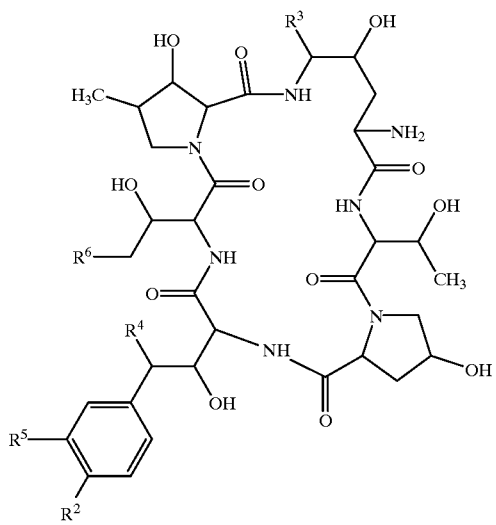

wherein $R^2$, $R^3$, $R^4$, $R^5$, and $R^6$ are as defined above.

7. The acylase according to claim 6, wherein $R^5$ is hydroxysulfonyloxy and $R^6$ is carbamoyl.

8. A method of producing a cyclic peptide compound of the formula [II]

[II]

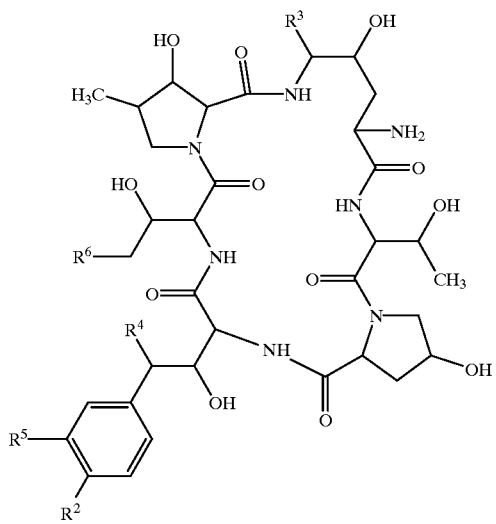

wherein $R^2$, $R^1$, $R^4$, $R^5$, and $R^6$ are the same groups as respectively defined below or a salt thereof, which comprises contacting a cyclic lipopeptide compound of the following general formula [I]:

[I]

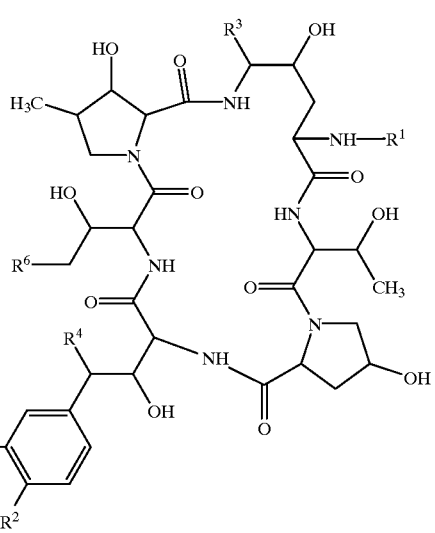

wherein $R^1$ is acyl;

$R^2$ is hydroxy or acyloxy;

$R^3$ is hydrogen or hydroxy;

$R^4$ is hydrogen or hydroxy;

$R^5$ is hydrogen or hydroxysulfonyloxy; and $R^6$ is hydrogen or carbamoyl or a salt thereof, in an aqueous solvent with the acylase of claim 3.

9. The method according to claim 8, wherein $R^5$ is hydroxysulfonyloxy and $R^6$ is carbamoyl.

* * * * *

UNITED STATES PATENT AND TRADEMARK OFFICE
CERTIFICATE OF CORRECTION

PATENT NO.    : 6,207,434 B1  
DATED         : March 27, 2001  
INVENTOR(S)   : Ueda et al.

Page 1 of 1

It is certified that error appears in the above-identified patent and that said Letters Patent is hereby corrected as shown below:

<u>Title page,</u>
Item [22] should read as follows:

[22] PCT Filed: Mar. 6, 1997

Signed and Sealed this

Sixteenth Day of October, 2001

*Attest:*

NICHOLAS P. GODICI
*Attesting Officer* — *Acting Director of the United States Patent and Trademark Office*

SEQUENCE LISTING

<160> NUMBER OF SEQ ID NOS: 2

<210> SEQ ID NO 1
<211> LENGTH: 20
<212> TYPE: PRT
<213> ORGANISM: Streptomyces sp.6907

<400> SEQUENCE: 1

Ser Asn Ala Val Ala Phe Asp Gly Ser Thr Thr Val Asn Gly Arg Gly
 1               5                  10                  15

Leu Leu Leu Gly
            20

<210> SEQ ID NO 2
<211> LENGTH: 20
<212> TYPE: PRT
<213> ORGANISM: Streptomyces sp.6907

<400> SEQUENCE: 2

Gly Ser Gly Leu Ser Ala Val Ile Arg Tyr Thr Glu Tyr Gly Ile Pro
 1               5                  10                  15

His His Val Ala
            20